(12) United States Patent
Monstdt et al.

(10) Patent No.: US 7,524,322 B2
(45) Date of Patent: Apr. 28, 2009

(54) DEVICE FOR THE IMPLANTATION OF OCCLUSION MEANS

(75) Inventors: Hermann Monstdt, Bochum (DE); Hans Henkes, Essen (DE); Marion Denk, Bochum (DE)

(73) Assignee: Dendron GmbH (DE)

( * ) Notice: Subject to any disclaimer, the term of this patent is extended or adjusted under 35 U.S.C. 154(b) by 420 days.

(21) Appl. No.: 10/486,899

(22) PCT Filed: Aug. 13, 2003

(86) PCT No.: PCT/EP02/09063

§ 371 (c)(1),
(2), (4) Date: Jun. 23, 2004

(87) PCT Pub. No.: WO03/017852

PCT Pub. Date: Mar. 6, 2003

(65) Prior Publication Data

US 2004/0236344 A1    Nov. 25, 2004

(30) Foreign Application Priority Data

Aug. 27, 2001  (DE) .............................. 201 13 741 U
Jul. 24, 2002  (DE) ................................. 102 33 728

(51) Int. Cl.
*A61M 29/00*    (2006.01)

(52) U.S. Cl. ................. 606/200; 606/194; 606/213
(58) Field of Classification Search .................. 606/1, 606/108, 151, 198, 213, 200
See application file for complete search history.

(56) References Cited

U.S. PATENT DOCUMENTS

| 5,250,071 | A  | * | 10/1993 | Palermo ........................ 606/198 |
| 5,624,449 | A  | * | 4/1997  | Pham et al. ................... 606/108 |
| 5,749,894 | A  | * | 5/1998  | Engelson ...................... 606/213 |
| 5,800,455 | A  | * | 9/1998  | Palermo et al. .............. 606/191 |
| 5,925,059 | A  | * | 7/1999  | Palermo et al. .............. 606/191 |
| 5,941,888 | A  | * | 8/1999  | Wallace et al. ............... 606/108 |
| 6,193,728 | B1 | * | 2/2001  | Ken et al. ..................... 606/108 |
| 6,589,230 | B2 | * | 7/2003  | Gia et al. .......................... 606/1 |
| 6,623,493 | B2 | * | 9/2003  | Wallace et al. ............... 606/151 |

* cited by examiner

*Primary Examiner*—Michael J. Hayes
*Assistant Examiner*—Michael G. Mendoza
(74) *Attorney, Agent, or Firm*—Berliner & Associates (57) ABSTRACT

The invention relates to a device for the implantation of electrolytically releasable occlusion means in body cavities or blood vessels.

The device is intended for use in veterinary or human medicinal processes for the occlusion of aneurysms.

34 Claims, 7 Drawing Sheets

DEVICE FOR THE IMPLANTATION OF OCCLUSION MEANS

The invention relates to a device for the implantation of electrolytically releasable occlusion means in body cavities or blood vessels.

The use of endovascular techniques for the occlusion of body cavities or vessels such as arteries, veins, fallopian tubes or vascular deformities such as, for example, vascular aneurysms is known in the art. In this case, the occlusion means is usually introduced by means of an insertion aid through a catheter into the cavity to be occluded and deposited therein.

The severance of the occlusion means necessary for the deposit thereof is in particular technically problematic, since the device required for this must on the one hand be as small as possible in design in order to be guided through the fine bore of the catheter to its destination, while, on the other hand, it must bring is about a reliable severance of the occlusion means since otherwise on withdrawal of the catheter there might be an unintended removal of the occlusion means from the cavity to be occluded and thus injury and/or rupture of the wall of the cavity or vessel may occur.

Mechanical methods intended to separate the occlusion means from the insertion aid do not take much time to perform, however the rigidity necessitated by technical design of the connection means between the occlusion means and the insertion means will impede the introduction of the implant. Furthermore, the low load-carrying capacity of the connection due to its rigidity entails a significant risk of premature detachment of the insertion aid from the occlusion means to be implanted. Moreover, for the purpose of separating the inserting wire and the occlusion means mechanically energy must be transmitted (as a rule by rotation of the inserting wire) by means of which the occlusion means to be implanted may become displaced leaving its desired location.

The electrolytic severance of stainless steel wire ends during transcatheter electro-coagulation of blood vessels or deformities of the same was initially described in 1979 by Thompson et al. and McAlister et al. (Radiology 133:335-340, November 1979, AJR 132:998-1000, June 1979).

Based on this method the European patent publication 0 484 468 describes a device for the implantation of an occlusion means involving the electrolytically corrodible design of the end of the guide wire at the connection between the guide wire and the occlusion means. This device expediently makes use of the electrical voltage applied to the occlusion means serving as an anode for electro-thrombozation for the simultaneous severance of the wire end and the attached occlusion means. As a result of the relatively massive design of the guide wire which is necessary to ensure the implant can be safely guided it is also quite difficult to suitably design the distal guide wire end intended to be severed in view of the need for a quick and thus safe severance of the elements:

For example, for the design of the guide wire exclusively materials can thus be employed which have an especially high degree of strength to enable the occluding wire to be reliably guided through the guide wire. For this reason, the selection of materials forming the point of electrolytic severance is extremely limited.

Moreover, it is also quite difficult to size of the point of detachment in such a way that renders it suitable for a quick severance: In devices for the electrolytic severance of occlusion means produced according to the state of the art the occlusion means and the guide wire do not form an integral unit but are usually connected mechanically. Such a design has the inherent disadvantage that in order to ensure sufficient strength in the proximal zone of the guide wire and for the purpose of rendering possible the electrolytic, corrosive severance of the wire end in the distal part of the wire the guide wire must be tapered toward its end by means of sophisticated grinding operations. This corrodible zone of the end of the guide wire at the connection location between the guide wire and the occlusion means must not, in order to ensure sufficient strength of the connection point, have a diameter below a certain minimum value of approximately 0.05 mm, since it is subjected to a high flexural load. Therefore, the corrodible wire end representing the connection point between occlusion means and guide wire is quite rigid and thus requires a relatively long time for its electrolytic, corrosive severance.

Since the prior art has not offered any possibility hitherto which is satisfactory as regards costs and safety for the endovascular deposit of occlusion means, it is the object of the invention to make available a device that enables occlusion means to be deposited in body cavities or vessels in an as fast as possible, most effective and reliable manner.

This object is to be achieved in accordance with the invention by a device for the implantation of occlusion means severable by electrolysis in body cavities or blood vessels comprising an insertion means and an occlusion means arranged at its distal end with the occlusion means being provided with an occlusion coil as well as, at one point, a form piece designed so as to be electrolytically corrodible so that while in contact with a body fluid the partial area of the occlusion means located at and connected to the distal end of the detachment point may be severed by electrolysis of the severance location.

Due to the fact that the electrolytically corrodible location of the device in accordance with the invention represents a part of the occlusion means itself it is subjected to considerably lower bending stresses during the implantation process than can be said of the customary, rigid electrolytically devised connections between guide wire and occlusion means. These lower bending stresses enable electrolytically corrodible spots to be used that have considerably smaller diameters than those known from the state of the art which leads to an improved and faster electrolytic severance of the occlusion means. Such diameters of less than 0.05 mm can be obtained by making use of suitable, e.g. mechanical methods.

A further advantage of the design of the electrolytically corrodible point in the inventive device in the occlusion means itself over the prior art method of severance of the guide wire end is the substantially wider choice of materials that can be employed to form the corrodible severance points. Unlike the conventional severance of the guide wire end the electrolytically corrodible point provided in the occlusion means of the device according to the invention does not have to be particularly robust so that it is possible to utilize less robust, more flexible materials provided they are corrodible and compatible with the body.

The occlusion means is, at least in part, designed in the form of an occlusion coil but may also on the whole have the form of a coil with the exception of the form piece serving as severance element.

At the proximal end of the occlusion means an insertion aid in the form of a guide wire is arranged. The separate guide wire offers the advantage that it may be produced from more cost-effective materials than those of the occlusion means, all the more so as it does not come into contact with body tissue. The physical form of the guide wire will preferably be such that it significantly enhances the control of the occlusion means by the catheter which results in improved placement characteristics.

In the case of such a design of the device according to the invention insertion aid and occlusion means are preferably joined together by soldering and/or adhesive and/or welding operations and/or by mechanical connections. These are connecting methods known in the prior art which are characterized by simplicity and strength of the connection so produced.

In a further expedient embodiment it is possible for the guide wire and the occlusion means of the device in accordance with the invention to be designed so as to form parts of the same wire. This embodiment is characterized by being particularly robust and may be cost efficient since the above mentioned step of connecting the guide wire to the occlusion means is dispensed with.

The occlusion means in this case is always provided with an electrolytically corrodible point in the form of a severance element or form piece:

The embodiment incorporating an electrolytically corrodible point in the occlusion means offers the advantage of being especially cost efficient from a manufacturing point of view and still offering the above described merits in comparison with devices fabricated according to the prior art and referred to above. Basically, the electrolytically corrodible point in this case may be arranged at any position of the occlusion means as thought technically expedient. The optimum position thereof may be simply determined by those averagely skilled in the art.

Embodiments comprising two or several electrolytically corrodible points in the occlusion means offer the additional advantage in that they enable variably sized lengths of the occlusion means to be separated and deposited for implantation in the body.

Furthermore, the integration of a plurality of electrolytically corrodible points in the occlusion means offers the advantage over conventional systems for the electrolytic severance of occlusion means that during an implantation operation it is not only one but several lengths of the same occlusion means that may be severed sequentially and placed in the cavity to be occluded. This is beneficial not only in terms of costs and time but also serves to further minimize surgery risks.

All the above mentioned conventional devices for the placement of occlusion implants suffer the disadvantage that exclusively implants can be detached or severed that have a predetermined length. As a rule, it is therefore necessary for the length, that is to say the longitudinal extent, of the occlusion means to be inserted to be predetermined directly prior to the placement of the implant based on the size of the cavity to be occluded. Since the irregular form of body cavities to be occluded makes it difficult to correctly assess the length of the occlusion means necessary for filling it may well be that the occlusions means inserted into the cavity to be occluded are either too long or too short so that on the one hand only an incomplete occlusion is achieved or, on the other, injury or rupture of the wall of the cavity or of adjacent vessels to be occluded may occur.

This embodiment of the invention with a plurality of electrolytically corrodible points is based on experiments carried out by the inventors which showed that when a current was applied to a device in accordance with the invention the surprisingly specific effect of severance occurred through electrolysis at the electrolytically corrodible point of the occlusion means next to the distal end of the catheter. This specifity is probably due to the fact that on the one hand the electrolytically corrodible points of the occlusion means in the catheter are isolated from the ionic medium through the catheter and thus are not undergoing electrolysis and, on the other hand, the current density decreases in proximal-distal direction owing to the distally increasing resistance in the occlusion means. As a result of this, the electrolytically corrodible point which, viewed in distal direction, is closest to the distal end of the catheter is subjected to the most intensive electrolytic process and is thus preferentially dissolved.

This embodiment of the device in accordance with the invention for the implantation of occlusion means combines, unlike any other prior-art device, the advantages of an efficient occlusion with low surgery risks and cost efficiency. The implant length which may be determined during the implanting procedure prevents an occlusion means of insufficient length to be placed in the cavity to be occluded which would otherwise lead to a thrombus of insufficient size for the space to be occluded. It may also be prevented that the occlusion means to be inserted into the cavity to be occluded is too long so that the danger of injury or rupture of the cavity to be filled or of adjacent vessels is minimized. Moreover, the severance of occlusion means by electrolytic methods is a proven technique whose parameters are substantially known. Just another point to be noted is that the device in accordance with the invention for the implantation of occlusion means makes it possible to advantageously employ standard lengths of occlusion means suitable for mass production. This constitutes a cost advantage over occlusion means of predetermined length as employed by conventional electrolytic or mechanical severance methods involving occlusion means of different length to be prepared which during the implantation operation are installed as a whole in the cavity to be occluded by severance of the wire end.

At least part of the occlusion means is designed in the form of a micro-coil. This design has an advantage in that a greater area is available for thrombosing.

For the same purpose it is also possible for other designs of the occlusion means to be employed which increase the area of the same and, for example, designs are feasible whose distal end is forked.

To ensure the most gentle and effective filling of the body cavity to be occluded a design of the device in accordance with the invention is advantageous that provides for an occlusion means or part thereof which is subject to an elastic biasing force so that after release from the catheter coils are formed by it. This design permits a dense and gentle filling of the cavity to be occluded without the occlusion means having to be shaped, by the wall of the cavity to be occluded, into forming such coils which diminishes the risk of a wall rupture. In case the occlusion means has the form of a coil or micro-coil secondary coils will form as a result of the elastic biasing force.

To imprint an elastic biasing force on the occlusion means or part thereof it is particularly preferred to provide the occlusion coil with a wire core made of a material having shape-memory properties. For example, materials having shape-memory properties are alloys containing titanium and nickel which are known by the name of Nitinol, as well as iron and copper based alloys. Shape-memory properties may be based on a stress-induced martensitic transformation or a temperature-induced martensitic transformation or may be the result of a combination of the two. Methods for the induction of shape-memory properties are known to those skilled in the art. Wires provided with a biasing force serve primarily as a kind of safety line which may be suitably employed to facilitate the withdrawal of already placed coils (before severance) into the micro-catheter.

In case a wire core of a material having shape-memory properties is integrated into the occlusion coil the coil will adapt to the pre-defined shape of the wire core. In this way, a predetermined spatial structure is achieved that may, for example, consist of a secondary coil. Geometric cage structures that enable an internal hollow space to form out have shown particular advantages in that the structure imprinted on the occlusion coil induces said coil to lean against the wall of the aneurysm. Examples of such cage structures are ball-shaped, cube, tetrahedron or prism structures. Further possibilities and examples include predetermined structures that initially provide for the aneurysm wall to be lined by the occlusion coil and subsequently result in the hollow space to be filled from the outside to the inside. For this purpose, especially secondary coil structures are suited which have a helix radius that is greater than the radius of the aneurysm to be treated.

A preferred form of the cage structure of an occlusion coil is based on a coil that has a meander-like form comprising, for example, 6 to 12 and in particular 8 to 10 bends or arcs. The meander structure itself is formed into a spatial structure having the individual bends or arcs of the occlusion coil extending uniformly over the inner wall of an imaginary ball, for example having a diameter ranging between 3 and 20 mm with a total length of the coil ranging between 40 and 250 mm. When such an occlusion coil is placed into an aciniform aneurysm of similar or identical size the aneurysm wall will be lined and/or strengthened by means of the coil structure. The remaining cage can then be filled with additional coils.

The above described wires having super-elastic or shape-memory properties can be connected with the severance element and the distal end of the occlusion means through cementing/gluing, welding, soldering or by mechanical methods. Preferred methods are laser welding and a mechanical connection achieved by the compact winding onto the severance element, analogously to the attachment of the spirals/coils on the guide wire and severance element. In this manner, the occlusion means and wire form a constructive unit the overall characteristics of which are determined by the properties of the individual elements.

After the external constraint (e.g. through a catheter lumen) has been removed the material bond comprising coil/spiral (Pt or Pt alloy) and the filament (NiTi) can be designed in such a way that the stretching force from the predetermined structure to the guided structure may be significantly influenced both by the properties of the coil/spiral and by the properties of the filament. In this way, for example, the force portion assignable to the coil may contribute 1% to 99% to the guided structure and that of the filament 99% to 1%. Preferably, the proportion of forces are balanced out such that, for instance, the portion assignable to the coil ranges between 25 and 75%, in particular between 40 and 60% while that assignable to the filament ranges between 75 and 25% and in particular between 60 and 40%. Such a variation may be brought about by an appropriate dimensioning of the components and/or through a suitable thermal treatment of both components.

It may be quite expedient for the electrolytically non-corrodible section(s) of the occlusion means to contain one or more of the following materials: noble metals or noble metal alloys, preferably platinum or platinum alloys.

Also preferred is an embodiment of the device according to the invention that comprises a severance element/form piece made of stainless steel.

Moreover, the stainless steel grades of type AISI 301, 303 or 316 and/or subgroups of these types are particularly suited.

The stainless steel grades that may be used for such form pieces preferably have a chromium content X of $12 \leq x \leq 20\%$ by weight. Examples in this case are steel grades 1.4410, 1.4310, 1.4301 and 1.4122. Suitable, for example, are chromium-nickel steels of grade 18/8.

Another group of suitable steels are N-alloyed austenitic steels of stainless quality, in particular those stemming from the group of steels nitrogen-hardened under pressure.

The corrosion behavior of austenitic stainless steels of the above mentioned grades can be influenced by an appropriate after-treatment. Especially by heat treatment their structures may be modified such that, for the purpose of the invention, they are rendered well electrolytically corrodible in an extraordinarily effective way, i.e. they are caused to rapidly disintegrate by applying an electric voltage in an electrolyte such as blood. Taking the thicknesses herein intended for use such disintegration occurs within a time span of less than 1 minute, in particular within a time span of less than 30 seconds.

The heat treatment required for this can be carried out with the help of a laser, in a customary furnace or by means of an induction coil. The temperature range required for this is approximately 500 to 1000° C., preferably 600 to 950° C. and in particular 700 to 900° C. It is assumed that such a heat treatment causes recrystallization accompanied by the formation of large microstructural grains and hard metal carbides which results in the grain boundary stability to diminish. The formation of chromium carbides segregating at the grain boundaries leads to a chromium depletion of the matrix and furthermore brings down the resistance to intergranular corrosion. This will quickly enlarge the surface available for corrosion so that the structure will rapidly decompose under the influence of a current applied within an electrolyte.

A homogeneous heat treatment in a furnace in the temperature ranges referred to above is preferred, and in the event of higher temperatures the time span provided for the treatment may be shortened; however, a heat treatment by means of a laser is preferred as well.

In accordance with an advantageous embodiment of the invention combinations of materials are selected for forming the electrolytically non-corrodible sections at the transitions to the electrolytically corrodible form piece that are suitable for forming local elements. In this manner—and irrespective of whether the diameter at the corrodible points is reduced—the electrolytic detachment capability of the occlusion means is improved.

The most suitable material combinations to this effect are those in which for forming the electrolytically corrodible points stainless steels with noble metals or noble metal alloys, in particular Pt, Pt metals, Pt alloys, Au alloys or Sn alloys, are present. Preferably, the form piece is encased on both sides by platinum coils or coils of platinum alloys.

The use of the above mentioned materials for the formation of the electrolytically non-corrodible section or sections and of the electrolytically corrodible point or points of the occlusion means ensures the specific electrolytic corrosion of the occlusion means on the intended form piece in a very short time.

It is particularly beneficial to shape out electrolytically corrodible points with form pieces forming out local elements on either side. This embodiment of the electrolytically corrodible points is substantially more susceptible to corrosion and therefore corrodes substantially more rapidly than form pieces that form a local element on one side only. Therefore, it is preferred to utilize material combinations that are maximally spaced apart in the electrochemical series. This as well is an advantage of the device in accordance with the invention over devices known in the prior art that provide for the end of the guide wire to corrode to bring about the severance of the embolizing wire since in this case it is merely to one side, namely on the embolizing wire side (said wire usually being made of platinum), that a local element is formed.

The electrolytically corrodible form pieces are expediently designed to meet functional requirements. It is thus advantageous with regard to the flexural or bending load to adapt the form of the electrolytically corrodible form piece to the form of the occlusion means and integrate said piece, for example, into the turns of an occlusion means shaped as micro-coil. On the other hand, an essentially straight form of the electrolytically corrodible form piece offers the advantage of being less sophisticated from a technical viewpoint. To enhance the sliding capability of the occlusion means in the catheter it is advantageous to have an alignment of the essentially straight electrolytically corrodible form piece along the longitudinal axis of the occlusion means.

As provided for by the invention, the electrolytically corrodible point on the occlusion means may, for example, be a form piece placed between the electrolytically non-corrodible portions of the occlusion means. This embodiment offers the advantage that in this case a particularly large number of different materials may be combined with one another for the formation of the electrolytically corrodible point and the electrolytically non-corrodible sections. This embodiment is furthermore advantageous in that the electrolytically corrodible point and the electrolytically non-corrodible sections may be joined together in a modular and thus technically non-sophisticated fashion. This is especially simple if the electrolytically corrodible point and thus the form piece which constitutes it is essentially straight.

The form piece constituting the electrolytically corrodible point may be expediently connected to the non-corrodible sections by soldering and/or cementing/gluing and/or welding operations. It is likewise possible for the form piece constituting the electrolytically corrodible point to be mechanically attached to the electrolytically non-corrodible sections, for example by clamping or crimping in position, provided the electrolytically non-corrodible sections possess recesses to accommodate said form pieces. This is the case, for instance, with electrolytically non-corrodible sections formed by micro-coils encircling an inner cavity. In this manner, the form pieces may be inserted and secured in said cavity thus having positive-fit characteristics. In this context it may also be expedient for the form-piece receiving outer parts of the electrolytically non-corrodible sections designed as micro-coil to be reinforced. It is particularly preferred here to weld the form piece to the occlusion means on both sides.

In this respect it is especially advantageous for the form piece constituting the electrolytically corrodible point to be pre-corroded by etching or other methods so that the diameter thereof tapers toward the center. The outer and thus weakened portions of the form pieces of larger diameter are then joined to the electrolytically non-corrodible sections by, for example, non-autogenous welding, mechanical insertion or cementing/gluing. Therefore, the connection between the electrolytically corrodible point and the electrolytically non-corrodible sections is extremely robust whereas the diameter tapering towards the middle of the form piece due to pre-corrosion causes the occlusion means being easily detachable by electrolytic action. If platinum alloys or platinum metals are employed as material for the formation of the electrolytically non-corrodible sections which are to be combined with stainless steel as a material of the form piece constituting the electrolytically corrodible point a joining method by non-autogenous welding is particularly preferred.

It may be expedient in this respect to provide the form piece with a partial coating consisting of a material that in the electrochemical series is located above the one constituting the form piece. This embodiment is particularly advantageous with respect to the corrodibility of the electrolytically corrodible points which are located in non-coated places on the form piece. Coatings of Zn or Sn or alloys of these metals provided on form pieces made of stainless steel were found to be particularly beneficial.

The mechanical attachment of the form piece is of special benefit if the electrolytically corrodible point is primarily of straight configuration and located along the longitudinal axis of the occlusion means. In this case, the modules constituting the occlusion means (electrolytically non-corrodible sections and the electrolytically corrodible point) can be joined very easily from a technical viewpoint.

To further improve the securing and stability of the individual modules constituting the occlusion means it is also possible to adopt a combination of the above mentioned methods.

The flexibility of the occlusion means is also ensured when fitted together mechanically due to the selection of materials and as a result of the small diameter of the form pieces constituting the electrolytically corrodible points.

In one embodiment of the device according to the invention the form piece constituting the electrolytically corrodible points is designed as a micro-system component. Said piece may, for instance, be designed as an elongated micro-system component the diameter of which tapering towards the middle. The insertion of said micro-system components is achieved by making use of the customary methods referred to above. The use of such micro-system components tapering toward the middle offers the advantage that the areas of the largest diameter are attached to the electrolytically non-corrodible sections and thus ensure the parts are firmly bonded. On the other hand, the tapering area of smaller diameter is exposed to the surrounding medium and may readily be corroded electrolytically. In this manner, electrolytically corrodible points of especially small diameter may be produced.

Preferred embodiments of the electrolytically corrodible form piece used according to the invention are, for example, elements that comprise a plurality of stainless steel wire strands of small diameter, approximately 2 to 20 ultra-thin stainless steel wires which may also be braided to form a rope or cable structure. Preferred micro-structures are structured wires having, for example, holes, notches, recesses or the like, as well as micro-structure components in the form of stainless steel profiled parts of double T-shaped, cross-like, three-wing or other cross section. The primary goal to be achieved here is to enlarge the surface available for electrolytic corrosion. Especially preferred in this case is of course the combination of such structures with the weakening of the structure as explained above by means of thermal, chemical or electrochemical processes.

In the interest of enhancing corrodibility the taper in diameter of the electrolytically corrodible points towards the middle may also be expediently provided for other designs of the electrolytically corrodible points.

The diameter of the form piece of the device in accordance with the invention is expediently selected such that it warrants adequate stability on the one hand and, moreover, causes the electrolytically corrodible point to be electrolytically well corrodible in situ. Advantageous embodiments in this respect are those that, at the electrolytically corrodible point or points, provide for diameters of the occlusion means ranging between 0.01 and 0.05 mm, preferably 0.02 and 0.04 mm and particularly preferred 0.03 mm. For the electrolytically non-corrodible sections of the occlusion means, however, greater diameters may be selected.

In another beneficial embodiment the end of the guide wire and/or the adjacent part of the occlusion means and extending up to the form piece is provided, for example, with an insulating material coating of poor corrodibility or with a shrunk-on sleeve coat so that it cannot be attacked electrolytically.

The device according to the invention is expediently provided with an X-ray reflecting marker which, in particular, is arranged distally to the guide wire. Such marker preferably consists of the proximal end of the occlusion means which is located between the guide wire and form piece and is constituted by a coil of platinum or a platinum metal. Especially preferred is a defined length of this coil or spiral of, for example, 1 cm or 3 cm so that it may be used for the precise positioning of such coil or spiral. For this purpose the marker is positioned in such a manner that it coincides with another marker in the distal zone of a micro-catheter so that it is ensured that the severance point which is constituted by the form piece is located outside the micro-catheter and when under the influence of an applied voltage is subjected to the corrosion process. Placement of the micro-catheter proper in relation to the point of use of the occlusion means is effected by conventional methods making use of the marking of the micro-catheter.

The device according to the invention is preferably intended for use in veterinary or human medicine and, more particularly, for the endovascular treatment of intracranial aneurysms and acquired or innate arteriovenous blood vessel malformations and/or fistulas and/or for the embolization of tumors by thrombozation.

Moreover, the invention relates to an occlusion means as described above as well as an inventive device that, furthermore, comprises a voltage source, a cathode and a catheter with the occlusion means being slidable in longitudinal direction within the catheter and serving as anode so that when in contact with a body fluid the occlusion coil or part thereof can be severed by electrolysis.

The invention is now described by way of examples as follows with reference being made to the figures showing the respective embodiments.

Figure 1A:
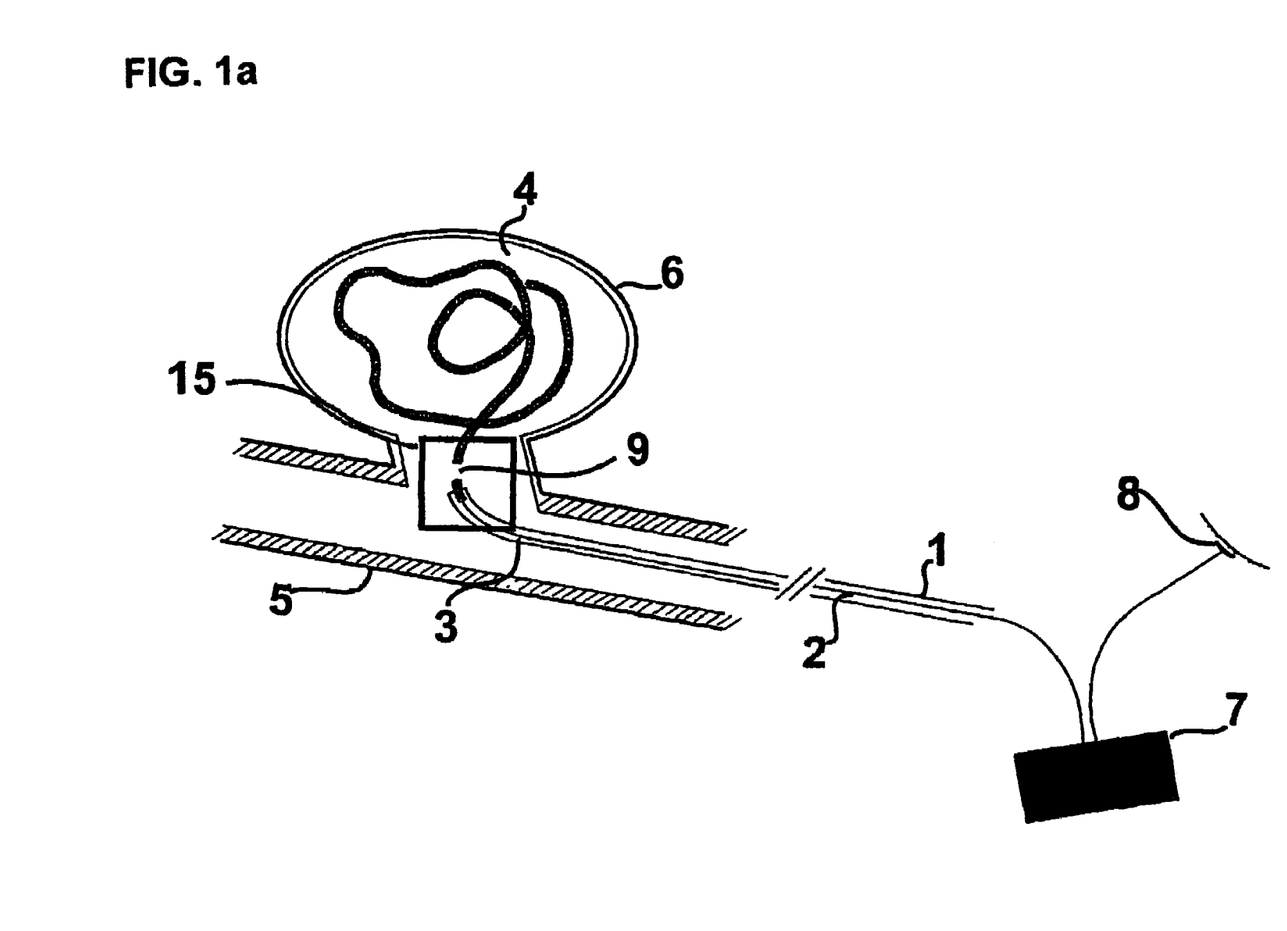
FIG. 1a shows a largely magnified vertical section of a micro-coil 3 positioned in an aciniform aneurysm including the respective device employed.
Figure 1B:
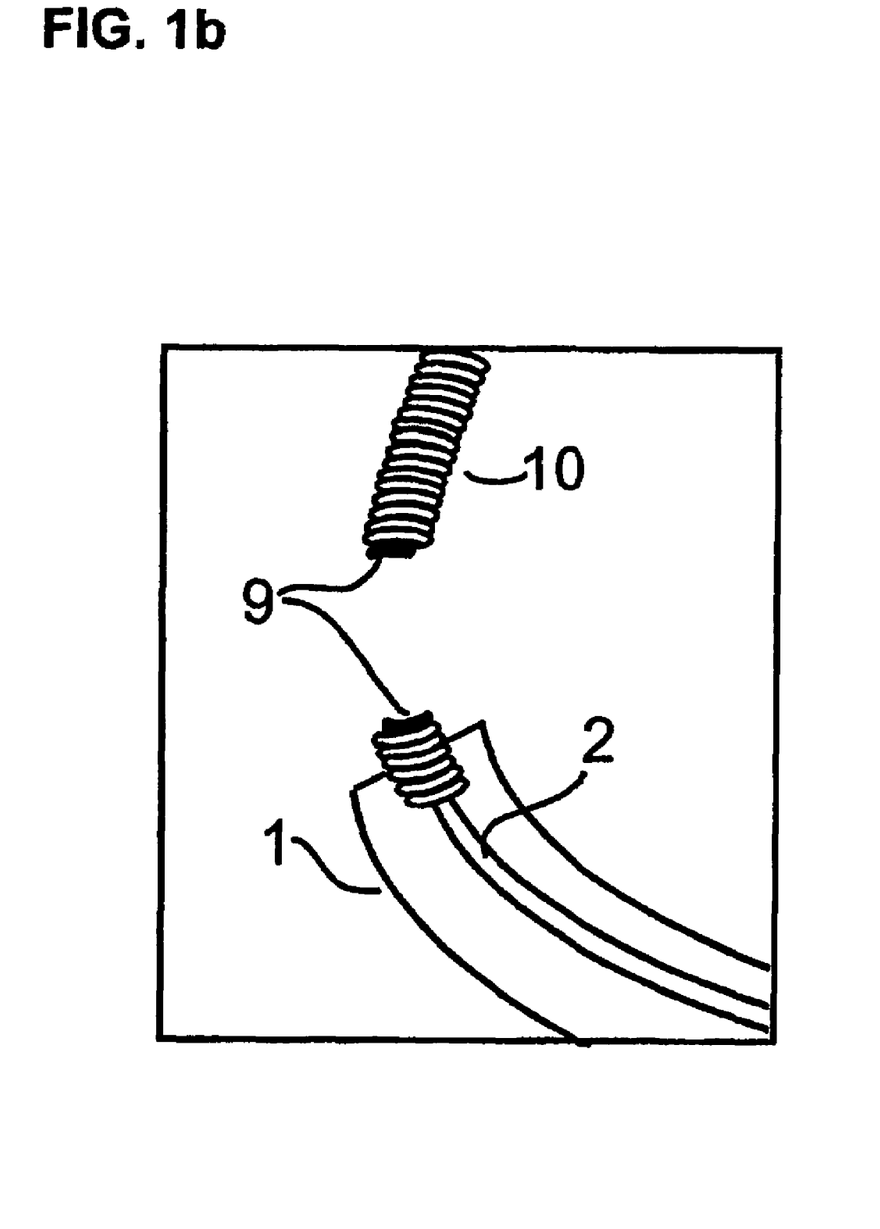
FIG. 1b shows the magnified section 15 of FIG. 1a illustrating the area of the electrolytically corrodible point 9 of micro-coil 3.

In FIG. 1a reference is made to a catheter 1, in particular to a catheter in the form of a flexible micro-catheter. An occlusion means 3 made of platinum metal alloy and designed in the form of a micro-coil is provided with electrolytically corrodible point 9/11 of stainless steel and is positioned, through micro-catheter 1, with the aid of the guide wire 2 at the mouth of the aneurysm 6 with said guide wire 2 being joined by a welding technique to the micro-coil 3. Since this connection produced by non-autogenous welding between the guide wire 2 and the first, proximal, electrolytically non-corrodible section of micro-coil 3 is not intended for electrolytic severance of the micro-coil 3 and, accordingly, does not need to have a particularly small diameter, it may be of particularly robust design. The use of stainless steel and platinum to produce the guide wire 2 on the one hand and, respectively, the micro-coil 3 on the other is particularly advantageous since the nickel constituent present in the steel combines very well with platinum during welding and thus forms an extremely smooth and robust joint. Due to the fact that guide wire 2 is moved in distal direction along the longitudinal axis of the micro-catheter 1 the micro-coil 3 is introduced into the aneurysm 6 and owing to its elastic biasing forms secondary coils or turns 4 on leaving the micro-catheter 1. Since the guide wire 2 and the micro-coil 3 can be moved in longitudinal direction in the micro-catheter 1 the portion to be implanted of the micro-coil 3 is introduced into the aneurysm 6 and the electrolytically corrodible point 9 located in the blood stream external to micro-catheter 1. The correct positioning is then performed, for example, under radiographic observance in accordance with suitable methods known in the art. Following this, with the aid of a source 7 of electrical power a voltage is applied for a period of 0.1 to 20 minutes to the cathode 8 positioned on the body surface and to the micro-coil 3 placed in the aneurysm 6 to be occluded and acting as anode. This brings about the electrolytic severance of that part of micro-coil 3 that is located in the blood, i.e. at the location of the electrolytically corrodible point 9 in the blood stream. FIG. 1 represents a micro-coil 3 whose electrolytically corrodible point 9 arranged closest to the distal end of micro-catheter 1 has already been severed by electrolytic corrosion. Reference number 15 identifies the area shown magnified in FIG. 1b.

FIG. 1b is a magnified view of a particular area of FIG. 1 illustrating the electrolytically corrodible point 9 already severed by electrolytic corrosion and located external to the micro-catheter 1. The occlusion means 3 in this case is initially attached to the guide wire 2 via section 10 which is electrolytically non-corrodible. In the distal direction another electrolytically non-corrodible section 10 is attached to the electrolytically corrodible point 9 of the occlusion means 3, said section 10 being placed into the aneurysm together with the remaining portion of the electrolytically severed electrolytically corrodible point 9 still adhering to it. The electrolytically corrodible point 9 of this example is adapted to the shape of the micro-turns 19 of the micro-coil 3.

Figure 2A:
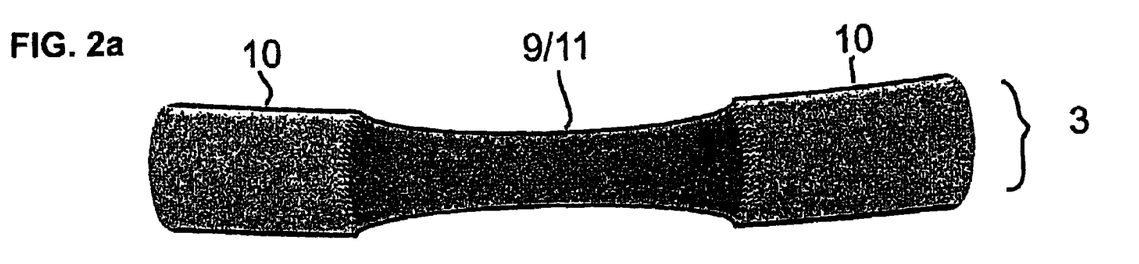
FIGS. 2a to c show on a more magnified scale than FIG. 1 three possible arrangements of electrolytically corrodible points 9 and electrolytically non-corrodible sections 10 in micro-coil 3 in accordance with the invention.
Figure 2B:
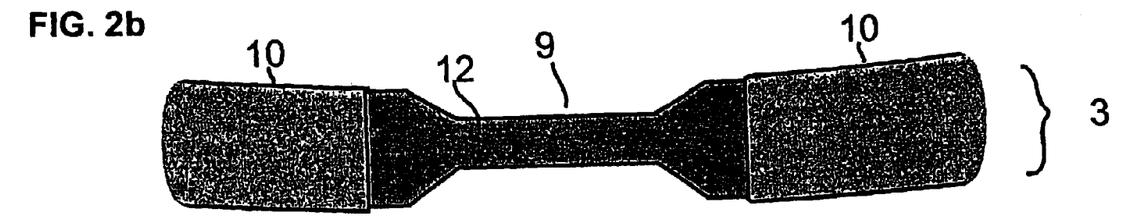
Figure 2C:
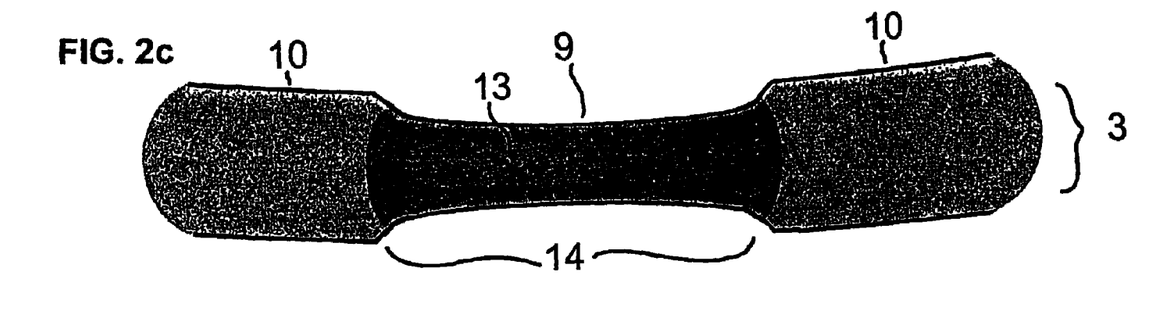

FIGS. 2a to c show on a scale more magnified than in FIG. 1 a section of three different embodiments of the micro-coil 3 in accordance with the invention.

FIG. 2a shows a micro-coil 3 having one or a plurality of non-corrodible sections 10 made of a platinum alloy to which a stainless steel form piece 11 0.03 mm in diameter is attached by welding methods thus constituting the electrolytically corrodible point 9.

FIG. 2b shows a portion of a micro-coil 3 according to the invention including a micro-system component 16 as electrolytically corrodible point 11, said component being arranged by a cementing/gluing process between the electrolytically non-corrodible sections 10.

FIG. 2c shows a portion of a micro-coil 3 comprising a stainless steel core 13, 0.03 mm in diameter. This stainless steel core 12 is surrounded by a coating of an electrolytically corrosion resistant material 14, said coating being provided with interruptions at regular intervals where the stainless steel core is accessible from the outside and thus forms an electrolytically corrodible point 9.

Figure 3A:
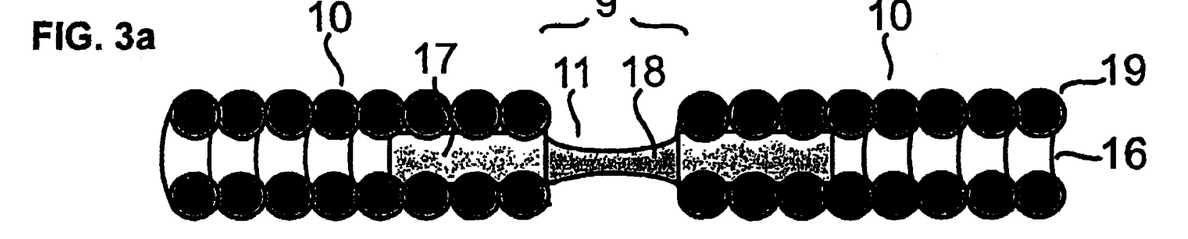
FIG. 3a to c show on a more magnified scale than FIG. 1 three possible arrangements of electrolytically corrodible points 11 and electrolytically non-corrodible sections 10 in the micro-coil 3 according to the invention with the electrolytically corrodible point 9 being arranged along the longitudinal axis of micro-coil 3.
Figure 3B:
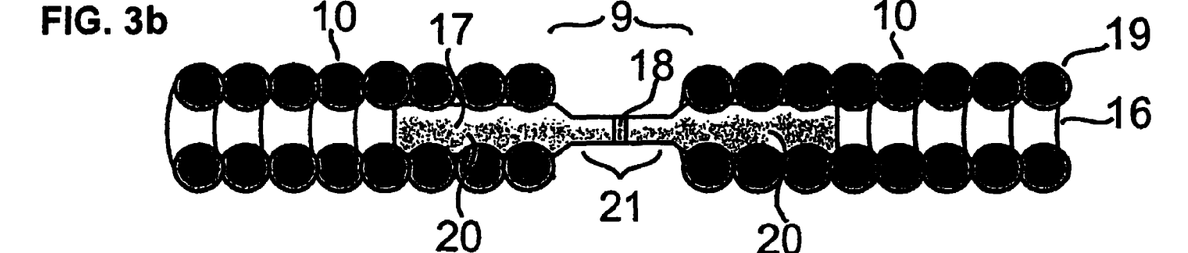
Figure 3C:
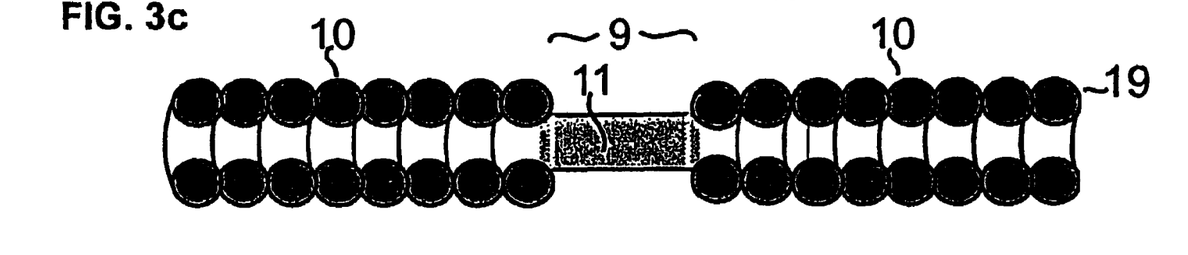

FIGS. 3a to c are part views on a more magnified scale than in FIG. 1 of three different embodiments of the micro-coil 3 of the invention having an electrolytically corrodible point or points 9 arranged along the longitudinal axis of micro-coil 3.

FIG. 3a shows a micro-coil 3 having a substantially straight form piece 11 of stainless steel material which is fitted in an interlocking fashion in the interior space 16 of the micro-turns 19 of platinum wire. The modular linking of electrolytically non-corrodible sections 10 of platinum-wire micro-turns 19 and of essentially straight form pieces 11 enables an electrolytically corrodible point 9 to be formed where the essentially straight form piece 11 is not surrounded by the platinum metal micro-turns 19 and is thus accessible from the outside. On the other hand, the non-corrodible sections 10 of the micro-coil 3 are made up by the platinum wire wound so as to form micro-turns 19 and fitted around either side of the essentially straight stainless steel form piece 11 in a mechanically interlocking manner. Form piece 11 is surrounded by an Sn layer 17 which is removed in the middle as a result of pre-corrosion. In view of this, the pre-corroded middle part 18 constituting the electrolytically corrodible point 9 of the form piece 11 is particularly susceptible to electrolytic corrosion since it has a very small diameter and forms local elements on both sides owing to the Sn coating 17.

FIG. 3b also shows a modularly designed micro-coil 3 whose micro-turns 19 of the platinum wire are fitted in an interlocking manner around the ends of a micro-system component 11 made of stainless steel and thus form the electrolytically non-corrodible sections 10 between which the exposed section of the micro-system component 11 constitutes the electrolytically corrodible point 9. The insertion of the sections of the micro-system component 11 with a larger diameter 20 in the inner space 16 of the platinum-wire micro-turns 19 ensures that the modular elements are held firmly together. On the other hand, the design of the electrolytically corrodible point 9 in the form of the tapered section 21 of the micro-system component 11 with smaller diameter offers greater flexibility and the advantage of an enhanced corrodibility of the electrolytically corrodible point 9.

This corrodibility is further improved by the design of the micro-system component consisting to a major extent of an Sn alloy 17 and a micro-severance element 22 arranged in the middle of the tapered section, said element 22 consisting of stainless steel and having an extremely small electrolytically corrodible point 9. This advantageous embodiment is highly corrodible and therefore most easily severed.

Alternatively, FIG. 3c shows a portion of a micro-coil 3 in accordance with the invention provided with an essentially straight form piece 11 of stainless steel forming the electrolytically corrodible point 9, said form piece being attached by welding methods to the micro-turns 19 of platinum wire forming the non-corrodible sections 10.

The disparities in electronegativity between the stainless steel forming the electrolytically corrodible point 9 and the platinum metal alloy forming the electrolytically non-corrodible sections 10 cause in an ionic medium such as blood the electrolytic severance of the electrolytically corrodible point 9 when electrical power is applied.

Figure 4:
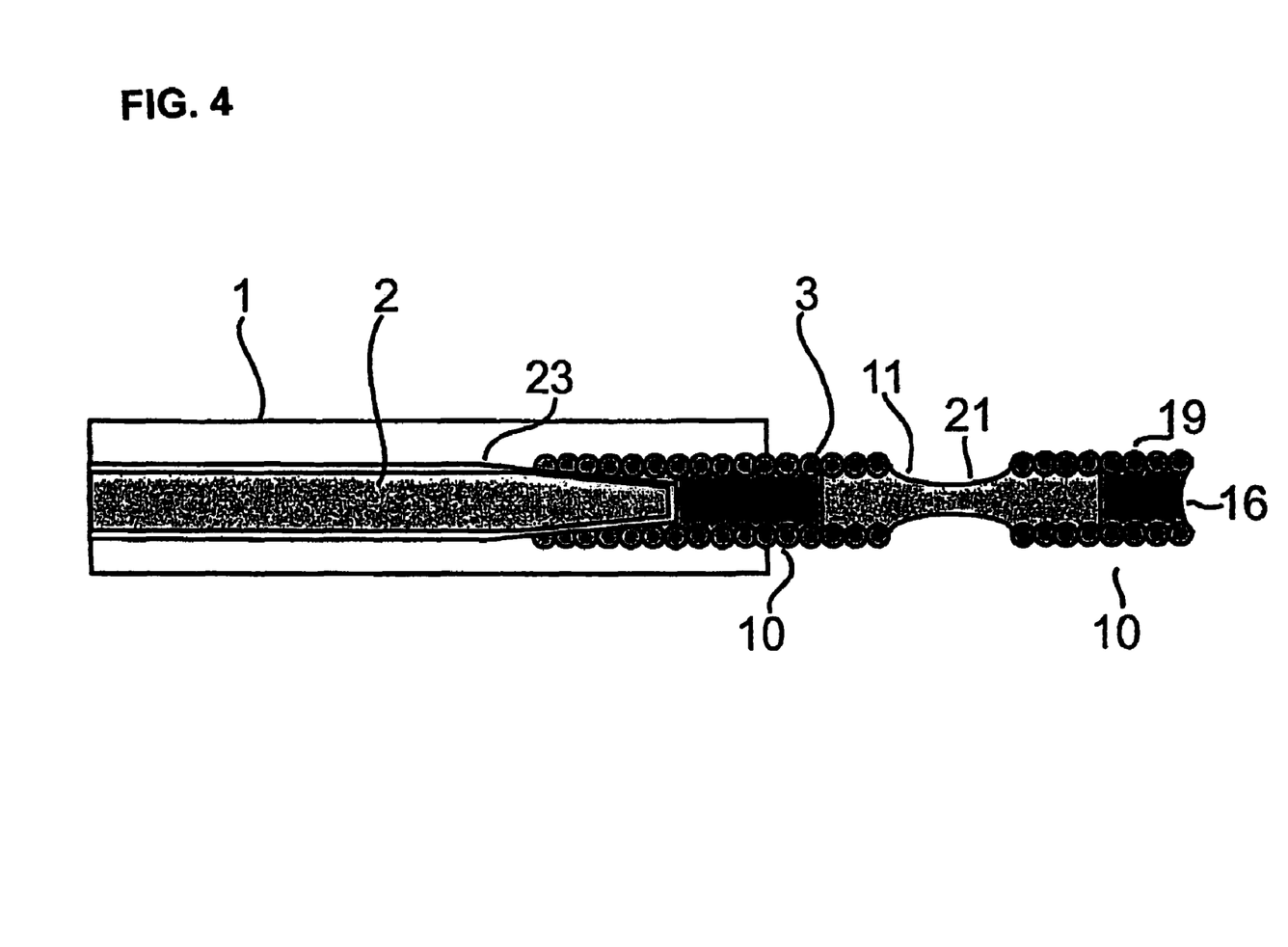
FIG. 4 is a longitudinal view showing how the guide wire 2 is attached to the micro-coil 3.

FIG. 4 is a longitudinal section of magnified representation through the transition segment between guide wire 2 and the occlusion coil 3. In this example the guide wire 2 is made up of high-strength stainless steel provided with a coating 23 which protects the steel material against corrosion. This coating can either be made to be non-conductive in which case the electrical current for the end of micro-catheter 1 is conducted to the occlusion coil 3 or part of the coating is non-corrodible but electrically conductive (for example a graphite coating) in which case the electrical current may also be routed via guide wire 2 into the micro-coil 3. In this example, the micro-coil 3 is constituted by the arrangement of a pre-corroded form piece 11 of stainless steel located between sections 10 of platinum wire which are electrolytically non-corrodible. The ends of form piece 11 are fitted mechanically into the inner space 16 formed by the platinum-wire micro-turns 19. Due to its reduced diameter 21 form piece 11 pre-corroded in the middle provides a point that is most easily corrodible electrolytically.

Figure 5:
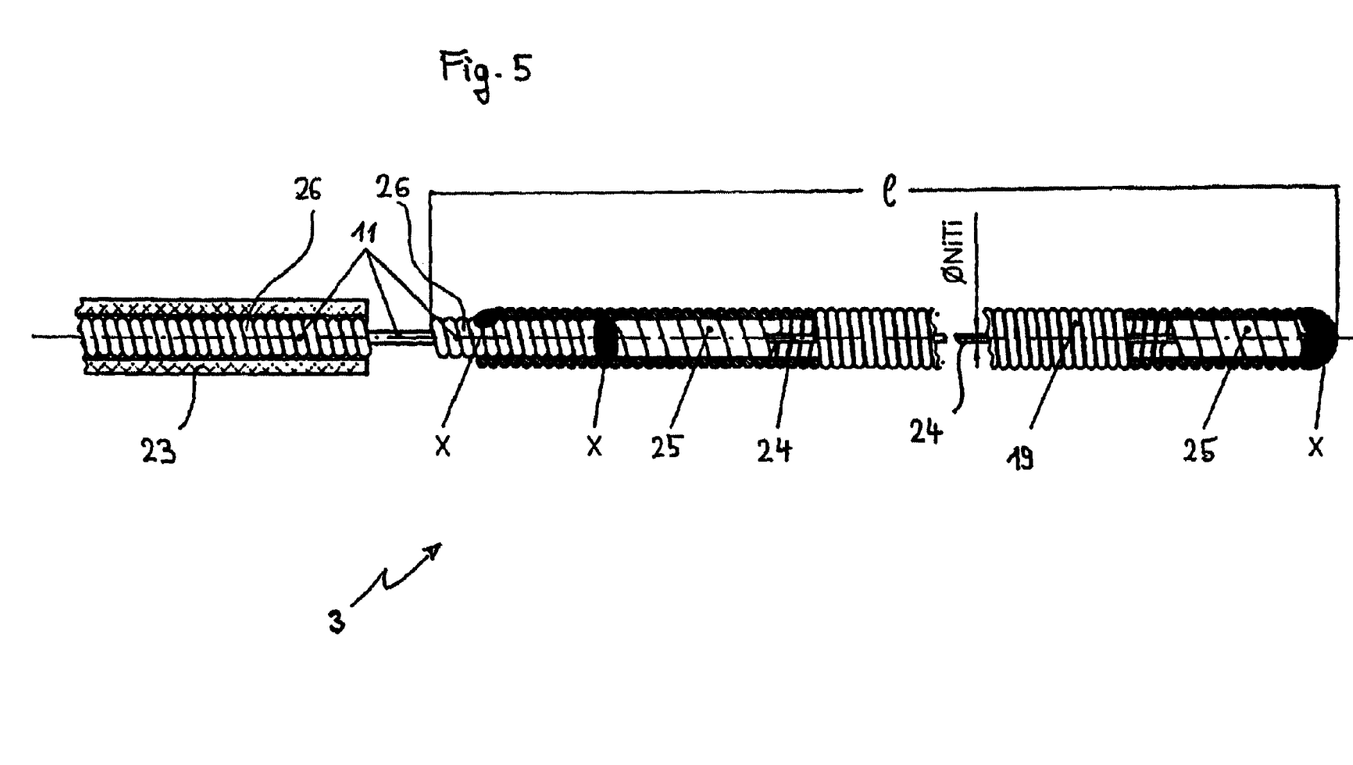
FIG. 5 is a representation of an occlusion means according to the invention showing occlusion coil and severance point 11.

FIG. 5 shows an occlusion coil 3 according to the invention provided with integrated severance element 11 embraced on either side by strengthening coils 26. Proximally, the strengthening coil 26 is provided with a coating 23, distally the strengthening coil 26 is linked to the actual occlusion coil 19.

After the occlusion coil has been detached at the severance location by electrical corrosion of the severance element 11, length L of the implant remains at the placement location. Aside from the coil made of platinum or platinum alloy 19 the occlusion coil itself consists of a central wire 24, which in this case is made of a nickel-titanium alloy and has super-elastic or shape-memory properties, serves as internal 'safety line' or, as the case may be, may be used to imprint on the coil a pre-determined spatial structure. Wire 24 is fixed at the proximal and distal end of the occlusion coil by laser welds X. Terminal spiral sleeves 25 serve to reinforce the occlusion coil in the end areas. The occlusion coil 19 is additionally secured by means of a laser weld X located at the strengthening coil 26. The strengthening coils 26 are preferably made of stainless steel.

Figure 6A:
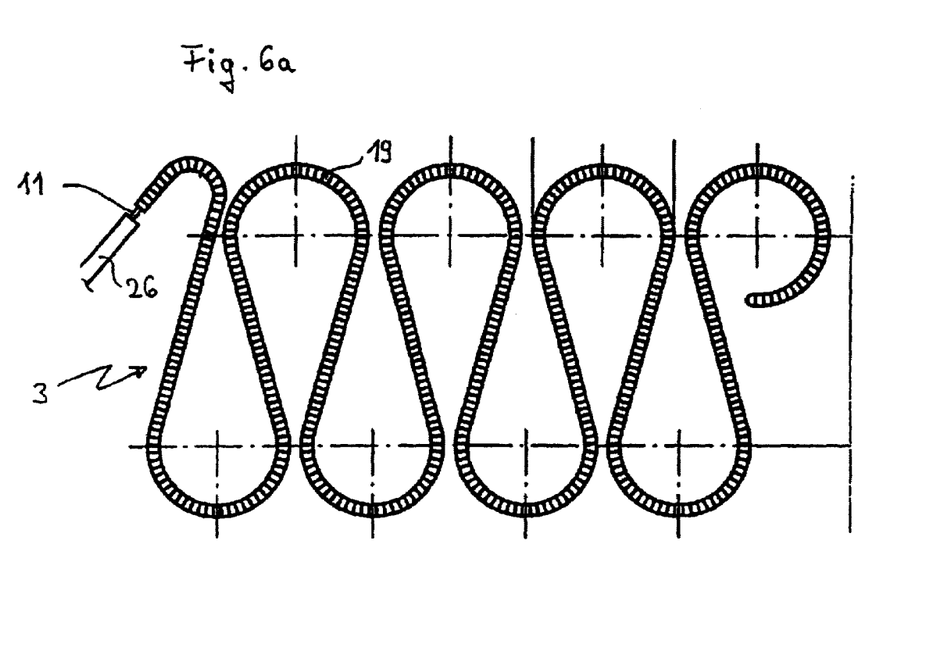
FIGS. 6a and b show an inventive occlusion coil having a meander structure imprinted on it, with (a) being a two-dimensional and (b) a spatial representation.

FIG. 6a shows an occlusion coil 3 in accordance with the invention provided with the coil 19, the severance point 11 and the proximally arranged strengthening coil 26 provided with a coating. In the two-dimensional view the occlusion coil itself has a meander-like structure forming a total of 8 bends. This structure is pre-determined through the shape-memory effect of the Nitinol wire provided within the coil and is formed into as soon as the coil is released from the constraint of the surrounding micro-catheter. Considering a total length of approximately 240 mm the bends, for example, have a diameter of 10 mm. The diameter of the coil may, for example, come to 0.15 mm, that of the Nitinol wire may be 0.05 mm.

At its distal and proximal end the occlusion coil preferably has a curved form so as to prevent a 'stiletto effect'. Furthermore, the distal end is rounded off by a weld point as shown in FIG. 5.

Figure 6B:
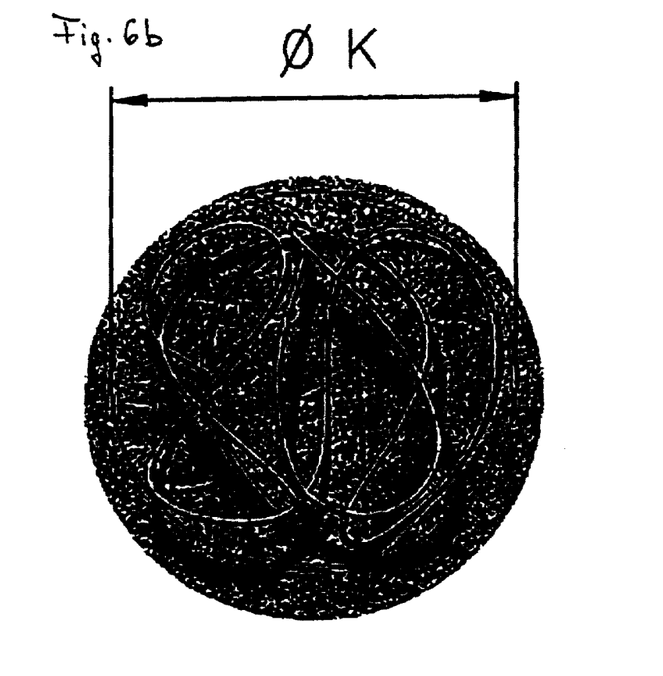

In FIG. 6b the coil illustrated in FIG. 6a is shown with the intended spatial structure it assumes when set free within an aneurysm. Having assumed its spatial structure the coil will lean to the inner walls of a ball simultaneously forming the loops imprinted on it. The diameter of the ball in the case illustrated amounts to approximately 20 mm.

The spatial structure shown in FIG. 6b may be imprinted on the occlusion coil shown with the aid of a tool having the shape of a cylinder or ball. For this purpose the occlusion coil is placed on the surface of the tool so as to form meander-like runs, fixed in that position and subjected to a customary shaping process involving treatment in a furnace. The material bond comprising a central Nitinol wire and a peripheral coil maintains its pre-determined structure after the heat treatment and always strives to assume this shape as soon as it is released from a micro-catheter.

The invention claimed is:

1. Device for the implantation of occlusion means severable by electrolysis in body cavities or blood vessels comprising a guide wire and an occlusion means arranged at its distal end characterized in that the occlusion means being provided with an occlusion coil of electrolytically non-corrodible sections as well as, at one point, a pre-corroded form piece containing large microstructural grains and hard metal carbides obtained by heat treatment and designed so as to be electrolytically corrodible.

2. Device according to claim 1, characterized in that the guide wire and occlusion coil are interconnected by one or more mechanical joining methods selected from the group consisting of soldering, cementing, gluing, and welding.

3. Device according to claim 1 characterized in that the occlusion coil or part thereof is designed in the form of a micro-coil.

4. Device according to claim 1, characterized in that the occlusion coil or part thereof is subject to an elastic biasing force so that it forms turns as soon as eternal constraints are removed.

5. Device according to claim 1, characterized in that the electrolytically non-corrodible sections of the occlusion coil consist of noble metal or noble metal alloys.

6. Device according to claim 1, characterized in that the electrolytically corrodible form piece of the occlusion coil consists of stainless steel or other corrodible material.

7. Device according to claim 6, characterized in that the form piece consists of stainless steel having a chromium content x of $12 \leqq =x \leqq =20\%$ by weight.

8. Device according to claim 6 or 7, characterized in that the stainless steel is of material grade 1.4410, 1.4310, 1.4301 or 1.4122.

9. Device according to claim 6, characterized in that stainless steel of type AISI 301, 304 or 316 or subgroups thereof is employed to produce the electrolytically corrodible form piece.

10. Device according to claim 6, characterized in that the form piece consists of an N-alloyed austenitic steel.

11. Device according to claim 1, characterized in that pre-corrosion has been effected by a heat treatment carried but at a temperature ranging between 500 and 1000° C.

12. Device according to claim 1 or 11, characterized in that precorrosion has been effected by a heat treatment carried out in a furnace/oven.

13. Device according to claim 1, characterized in that form piece is surrounded by elements ranking higher in the electrochemical series than the form piece so that local elements are produced.

14. Device according to claim 13, characterized in that the elements are of noble metal or noble metal alloys.

15. Device according to claim 5, 13 or 14, characterized in that the elements are micro-coils made of platinum or platinum metal alloys.

16. Device according to claim 1, characterized in that the shape of the electrolytically corrodible form piece conforms to the micro-turns of the occlusion coils.

17. Device according to claim 1, characterized in that the electrolytically corrodible form piece is connected to the occlusion coil by means of welding joints.

18. Device according to claim 1, characterized in that the form piece is a micro-system component.

19. Device according to claim 18, characterized in that form piece is a structured wire or a profiled element.

20. Device according to claim 1, characterized in that the portion of the occlusion means that is located between the distal end of the guide wire and the form piece consists of an x-ray reflecting material and serves as marker.

21. Device according to claim 20, characterized in that the portion of the occlusion means arranged between the distal end of the guide wire and form piece has a defined length and is formed by a platinum coil.

22. Device according to claim 1, characterized in that the distal end of the guide wire and/or the portion of the occlusion means arranged proximally to the form piece has been provided with a corrosion-preventing coating.

23. Device according to claim 1, 2 or 3, characterized in that the occlusion means comprises a central wire that connects the form piece with the distal portion of the occlusion means and consists of a material having super-elastic characteristics.

24. Device according to claim 4, characterized in that the occlusion coil is provided with a wire core made of a material having shape-memory properties, said core assuming, as soon as an external constraint acting on it is removed, a spatial structure imprinted on it.

25. Device according to claim 24, characterized in that the occlusion coil assumes, when the external constraint has been removed, the spatial structure imprinted on the wire core.

26. Device according to claim 24, characterized in that the spatial structure is a secondary coil or turn.

27. Device according to claim 24, 25 or 26, characterized in that the spatial structure is a geometric cage structure with/without an inner hollow space, particularly in the form of a ball, a cube, a tetrahedron or a prism.

28. Device according to claim 1, characterized in that it, furthermore, comprises a micro-catheter.

29. Device according to claim 28, characterized in that the micro-catheter has at least one marker element located in its distal area.

30. Device according to claim 1, characterized in that it comprises a catheter, a voltage source and a cathode, with the occlusion coil in the catheter being slidable in longitudinal direction and serving as anode so that when in contact with a body fluid the portion of the occlusion coil arranged distally to the form piece can be severed by electrolysis.

31. Device according to claim 17 in which the means of welding joints is by a laser welding method.

32. Device for the implantation of occlusion means severable by electrolysis in body cavities or blood vessels comprising a guide wire and an occlusion means arranged at its distal end characterized in that the occlusion means being provided with an occlusion coil as well as, at one point, a form piece of stainless steel having a chromium content x of $12 \leqq =x \leqq =20\%$ by weight, containing large microstructural grains and hard metal carbides obtained by heat treatment and designed so as to be electrolytically corrodible.

33. Device for the implantation of occlusion means severable by electrolysis in body cavities or blood vessels comprising a guide wire and an occlusion means arranged at its distal end characterized in that the occlusion means is provided with an occlusion coil as well as, at one point, a form piece of N-alloyed austenitic steel, containing large mircorstructural grains and hard metal carbides obtained by heat treatment and designed so as to be electrolytically corrodible.

34. Device according to claim 10 or 33 wherein the N-alloyed austenitic steel, is austenitic steel nitrogen hardened under pressure.

* * * * *

UNITED STATES PATENT AND TRADEMARK OFFICE
CERTIFICATE OF CORRECTION

PATENT NO. : 7,524,322 B2  
APPLICATION NO. : 10/486899  
DATED : April 28, 2009  
INVENTOR(S) : Monstadt et al.

Page 1 of 2

It is certified that error appears in the above-identified patent and that said Letters Patent is hereby corrected as shown below:

On the Title Pg, Item (75): Inventors, "Hermann Monstdt," should be changed to
--Hermann Monstadt,--

On the Title Pg, Item (30): Foreign Application Priority Data,
"Aug. 27, 2001 (DE).....................201 13 741 U" should be changed to
--Aug. 27, 2001 (DE).....................201 13 741.0--

Column 1, Line 18, "bring is about" should be changed to --bring about--

Column 1, Line 47, "for electro-thrombozation" should be changed to
--for electro-thrombolization--

Column 1, Line 53, "severance of the elements:" should be changed to --severance of the elements.--

Column 3, Line 14, "element or form piece:" should be changed to --element or form piece.--

Column 3, Line 61, "specifity is probably" should be changed to --specificity is probably--

Column 4, Line 59, "kind of safety line which" should be changed to --kind of "safety line" which--

Column 7, Line 15, "for example, be a" should be changed to --for example, a--

Column 9, Line 26, "tumors by thrombozation." should be changed to --tumors by thrombolization.--

Column 9, Line 47, "FIG. *3a* to *c* show" should be changed to --FIGS. *3a* to *c* show--

Column 13, Line 20, "as eternal constraints" should be changed to --as external constraints--

Column 13, Line 42, "carried but at" should be changed to --carried out at--

UNITED STATES PATENT AND TRADEMARK OFFICE
CERTIFICATE OF CORRECTION

PATENT NO. : 7,524,322 B2
APPLICATION NO. : 10/486899
DATED : April 28, 2009
INVENTOR(S) : Monstadt et al.

It is certified that error appears in the above-identified patent and that said Letters Patent is hereby corrected as shown below:

Column 14, Lines 59-60, "mircorstructural grains" should be changed to
--microstructural grains--

Signed and Sealed this

Fifteenth Day of September, 2009

David J. Kappos
*Director of the United States Patent and Trademark Office*